(12) United States Patent
Downs

(10) Patent No.: US 7,767,151 B2
(45) Date of Patent: Aug. 3, 2010

(54) HIGH THROUGHPUT MECHANICAL ALLOYING AND SCREENING

(75) Inventor: Robert Charles Downs, La Jolla, CA (US)

(73) Assignee: Wildcat Discovery Technologies, Inc., San Diego, CA (US)

( * ) Notice: Subject to any disclaimer, the term of this patent is extended or adjusted under 35 U.S.C. 154(b) by 205 days.

(21) Appl. No.: 11/197,180

(22) Filed: Aug. 3, 2005

(65) Prior Publication Data
US 2007/0031295 A1 Feb. 8, 2007

(51) Int. Cl.
*B01L 3/00* (2006.01)
(52) U.S. Cl. .......................... 422/102; 422/104; 422/99
(58) Field of Classification Search .................. 422/102, 422/104, 99; 435/305.2, 305.3, 305.4, 288.4
See application file for complete search history.

(56) References Cited

U.S. PATENT DOCUMENTS

| | | | |
|---|---|---|---|
| 3,591,362 A | 7/1971 | Benjamin | |
| 6,126,097 A | 10/2000 | Chen et al. | |
| 6,258,930 B1 | 7/2001 | Gauch et al. | |
| 6,350,414 B1 * | 2/2002 | Ballin et al. | ................. 422/101 |
| 6,514,478 B2 | 2/2003 | Zaluska et al. | |
| 6,667,009 B1 | 12/2003 | Desrosiers | |
| 6,817,558 B1 * | 11/2004 | Karlsson et al. | ............... 241/30 |
| 6,826,549 B1 | 11/2004 | Marks et al. | |
| 6,852,289 B2 * | 2/2005 | Gordon et al. | ............... 422/101 |
| 6,878,344 B2 * | 4/2005 | Mansky et al. | ............... 422/101 |
| 2005/0090019 A1 | 4/2005 | Wendelbo | |

FOREIGN PATENT DOCUMENTS

| | | |
|---|---|---|
| DE | 10125126 A1 | 11/2002 |
| EP | 1323472 A2 | 7/2003 |
| WO | WO03047744 A1 | 6/2003 |

OTHER PUBLICATIONS

Glen Mills Inc., Product Showcase: Planetary Ball Mill, www.glenmills.com/product_showcase/dry-fine-planetary.shtml.
Jensen, C. M and S. Takara, Catalytically Enhanced Systems for Hydrogen Storage, Proceedings of the 2000 Hydrogen Program Review.
Jensen, C.M. et al., Catalytically Enhanced Systems for Hydrogen Storage, Proceedings of the 2002 US DOE Hydrogen Program Review.
Gennari et al., Hydrogen Storage Using Mg Based Alloys Produced by Mechanical Alloying, Conference: "Renewable Resources and Renewable Energy: A Global Challenge", Jun. 10, 2004.

(Continued)

*Primary Examiner*—Jill Warden
*Assistant Examiner*—Natalia Levkovich
(74) *Attorney, Agent, or Firm*—Timothy L. Smith

(57) ABSTRACT

The invention provides an apparatus and methods for conducting ball milling operations in a high throughput manner. Also provided are devices and methods for high throughput screening of alloys and other materials to identify those that have desired gas storage properties.

11 Claims, 8 Drawing Sheets

OTHER PUBLICATIONS

Bossel et al., The Future of the Hydrogen Economy: Bright or Bleak?, 2003 Fuel Cell Seminar, Apr. 15, 2003.

Urretavizcaya et al., Mg-Ni Alloys for Hydrogen Storage Obtained by Ball Milling, Latin American Applied Research, 32: 289-294 (2002).

Dymatron, Inc., Megapact and Megamill-5 Multi-Role Laboratory Processing Equipment, http://www.dymatron.com/megamill.html.

Peterson Machine Inc., Attomill Sonic Ball Mill Grinder, OCETA Environmental Technology Profiles, http://www.oceta.on.ca/profiles/peterson/peterson_tech.html.

Retsch, Size Reduction and Homogenization with Ball Mills, Aug. 2004.

Lashkari, An automated multiplex oligonucleotide synthesizer: development of high-throughput, low-cost DNA synthesis, Proc. Nat'l. Acad. Sci. USA 92: 7912-7915 (Aug. 1995).

* cited by examiner

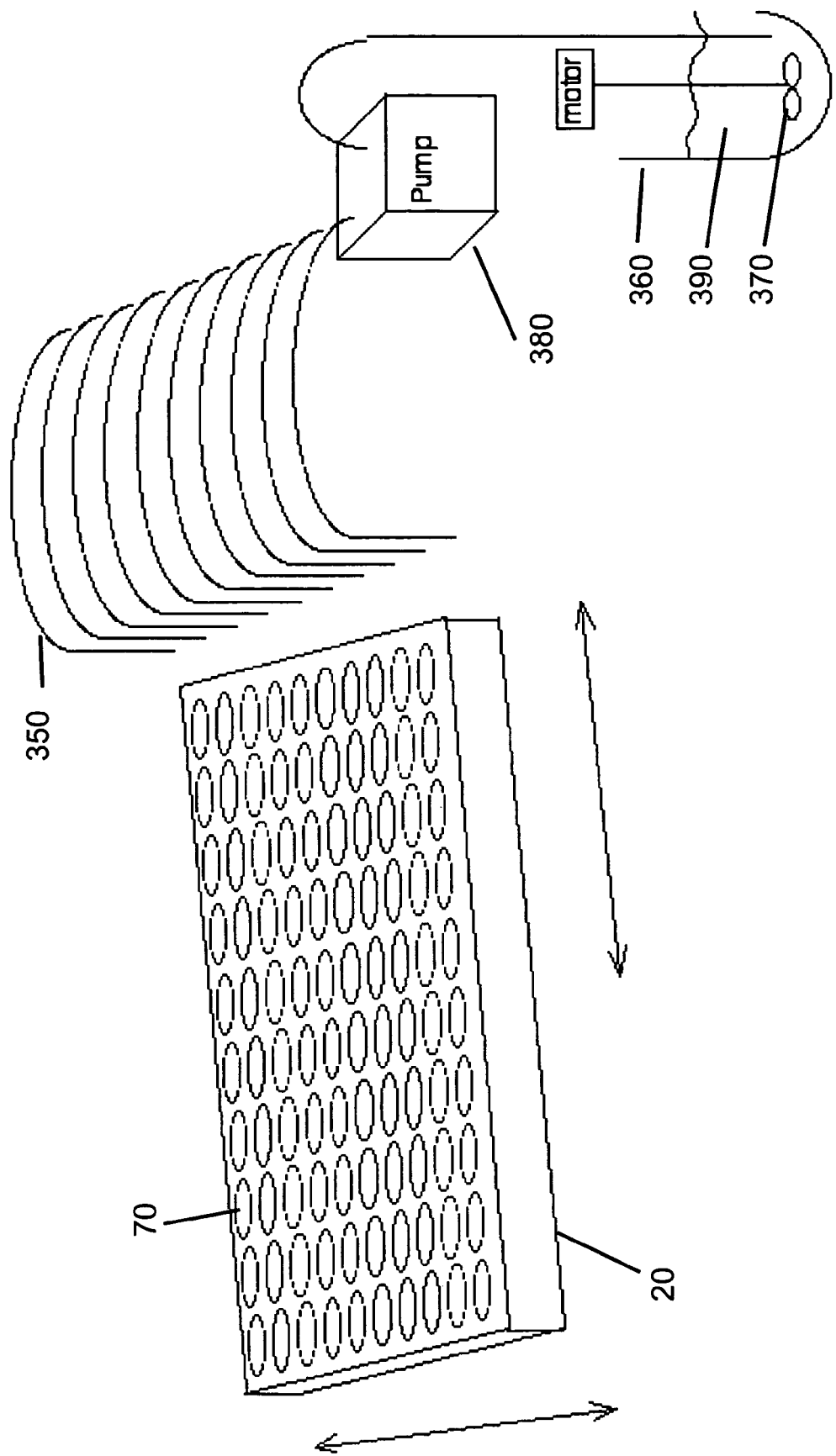

HIGH THROUGHPUT MECHANICAL ALLOYING AND SCREENING

BACKGROUND OF THE INVENTION

1. Field of the Invention

The present invention relates to an apparatus and methods for simultaneously producing multiple alloys of ultra-fine powder particles, and for high-throughput assaying of the alloys to identify those having desired gas storage properties.

2. Background

Materials science has shown that materials having a desired property can often be found by making a massive library of different materials from various combinations of precursor substances and assaying the resulting materials for the desired property.

One method that is suitable for making different materials is mechanical alloying, which was invented by J. S. Benjamin and is described in U.S. Pat. No. 3,591,362. Mechanical alloying involves forming alloys from pure starting materials by milling a mixture of the powders in a high energy ball mill. During the milling, the starting particles undergo repeated collisions with grinding balls, causing deformation, welding and fracture of the particles which result in microstructural refinement and composition changes leading to the formation of nanocrystalline or amorphous alloys. The process can result in two or more particulate starting substances becoming so intimately mixed that the resulting particulate product is either a true alloy or a remarkably homogenous blend, or a combination of a true alloy and a homogeneous blend.

Previously known devices and methods for mechanical alloying are not suitable for forming the massive libraries of materials that are necessary for optimal screening to identify materials that have desired properties. Therefore, a need exists for a mechanical alloying apparatus and methods for the production of large libraries of different materials in a high throughput manner. The present invention fulfills this and other needs.

SUMMARY OF THE INVENTION

The invention provides a multiwell ball milling fixture that is useful for performing multiple ball milling operations in a high throughput manner. In some embodiments, the fixture can be used not only for the ball milling, but also for further operations such as gas storage assays. The fixture includes a multiwell plate and a lid. The multiwell plate has a plurality of sample wells, each of which has a sidewall and a bottom wall. The bottom wall is preferably joined to the sidewall by a rounded edge. The lid defines a planar expanse sufficient to cover the sample wells and has a plurality of gas outlet ports. The gas outlet ports are positioned such that two or more of the sample wells are each in fluid communication with an associated gas outlet port when the lid is positioned on the multiwell plate. In some embodiments, the fixture also includes a cap that defines a planar expanse sufficient to cover each of the plurality of gas outlet ports when the cap is positioned on the lid. The fixture typically has one or more seals disposed between the multiwell plate and the lid, which seals allow gas flow between a sample well and an associated gas outlet port but prevent gas flow between sample wells and between a sample well and a non-associated gas outlet port. If a cap is used, the fixture generally has one or more seals disposed between the lid and the cap, which seals prevent gas flow from one gas outlet port to a second gas outlet port associated with a second sample well.

The lid of the multiwell ball milling fixtures can have a plurality of recessed areas which have a cross-sectional shape that corresponds to the cross-sectional shape of the sample wells. The positions of the recessed areas spatially correspond to the sample wells when the lid is placed on the multiwell plate. In some embodiments, the recessed areas have a concave top surface. For example, the top surface can have a curvature that is substantially similar in radius to the radius of the curved surface that joins the sidewall and the bottom surface of the multiwell plate.

The invention also provides a high throughput ball milling apparatus. This apparatus typically includes: (a) a rotary platform which rotates about a first axis, (b) a plurality of receptacles that are rotatably supported on the rotary platform, wherein each receptacle rotates about an axis that is substantially parallel to the first axis and is configured to hold at least one multiwell ball milling fixture; and (c) a motor means in drive relation to the rotary platform that provides rotational forces thereto. Each receptacle can hold at least one multiwell ball milling fixtures, and in many embodiments can hold two or more plates. The apparatus also has a motor or other means for driving rotation of the receptacles. The rotating platform and the receptacles can rotate at the same speed, or at different speeds.

Also provided by the invention are gas storage assay caps for a multiwell plate. The assay cap has a bottom surface and a top surface and includes: (a) a plurality of gas outlet ports that each have a first opening on the bottom surface and a second opening in a second surface of the cap, wherein the first openings of the gas outlet ports are spatially arranged such that each gas outlet port is in fluid communication with a sample well of a multiwell plate when the assay cap is positioned either (i) on a multiwell plate, or (ii) on a lid for a multiwell plate, which lid comprises a plurality of gas outlet ports that are in fluid communication with a sample well of a multiwell plate when the lid is positioned on a multiwell plate; and (b) a pressure sensor in fluid communication with the second opening of each of at least one of the gas outlet ports. Typically, each of the gas outlet ports is in fluid communication with a pressure sensor.

In some embodiments, gas storage assay cap is attached to a multiwell plate lid that has a bottom surface and a top surface and defines a planar expanse sufficient to cover sample wells of a multiwell plate. The lid has a plurality of gas outlet ports that each have a first opening on the bottom surface of the lid and a second opening in the top surface of the lid, wherein the first openings of the gas outlet ports are spatially arranged such that each gas outlet port is in fluid communication with a sample well of a multiwell plate when the assay cap is positioned on a multiwell plate, and the second openings are spatially arranged such that each gas outlet port in the lid is in fluid communication with a conduit in the assay cap. In some embodiments, the first opening of a gas outlet port in the multiwell plate lid is positioned in a recessed area that spatially corresponds to the sample wells when the lid is placed on a multiwell plate. The second openings of the gas outlet ports are in fluid communication with (a) a gas source, and (b) a vacuum source.

The invention also provides a high throughput gas storage assay device. These devices include: (a) a multiwell plate that has a plurality of sample wells; (b) a lid defining a planar expanse sufficient to cover the sample wells, which lid has a plurality of gas outlet ports, wherein the gas outlet ports are positioned such that two or more of the sample wells are each in fluid communication with an associated gas outlet port when the lid is positioned on the multiwell plate; and (c) an assay cap that defines a planar expanse sufficient to cover the gas outlet ports of the lid when the assay cap is positioned on the lids, wherein the assay cap includes a plurality of gas outlet ports that are positioned such that at least one gas outlet port in the cap is in fluid communication an associated gas outlet port in the lid.

In some embodiments, the gas storage assay device has a pressure sensor in fluid communication with each of the gas outlet ports. The device also can have a vacuum source and a test gas source, both of which are in fluid communication with the gas outlet ports of the assay cap. One or more valves that regulate gas flow between the gas outlets and the vacuum source, and one or more valves that regulate gas flow between the gas outlet ports and the test gas source can also be included in the gas storage assay device. A single valve can be used for switching between the test gas source, the vacuum source, and the pressure sensor being in fluid communication with the gas outlet port.

The gas storage assay device can also include a controller that comprises logic instructions that direct the device to perform a method that comprises the following steps:
  (a) open a valve between the vacuum source and the gas outlet port, thereby applying a vacuum to a sample well;
  (b) close the valve between the vacuum source and the gas outlet port;
  (c) open a valve between the test gas source and the gas outlet port, thereby allowing a test gas to flow into the sample well; and
  (d) close the valve between the test gas source and the gas outlet port.

Also provided by the inventions are methods for obtaining a plurality of alloys. These methods involve:
  (a) dispensing a plurality of mixtures of precursor substances into sample wells of a multiwell plate;
  (b) dispensing grinding balls into the sample wells; and
  (c) subjecting the multiwell plate to a ball milling operation to form a plurality of alloys in an ultrafine powder form.

The invention also provides a library of alloys in ultrafine powder form, wherein the library comprises at least 10 different alloys. In some embodiments, each of the members of the library is contained in a single multiwell plate. In some embodiments, the alloys of the library are formed by milling of a mixture of two or more precursor substances, wherein at least one of the precursor substances is a metal element. For example, in some embodiments at least one of the precursor substances is an element that can form a compound with hydrogen.

DESCRIPTION OF THE DRAWINGS

FIG. 4 shows a schematic diagram of an apparatus for dispensing materials into individual wells 70 of the multiwell plates 20 in a combinatorial manner.

DETAILED DESCRIPTION

The present invention provides an apparatus for simultaneously producing multiple alloys that consist of ultra-fine powder particles. Also provided are apparatus and methods for assaying alloys to identify those that have desired gas storage properties. The apparatus and methods are useful for, for example, creating and identifying alloys that are capable of storing gases such as hydrogen.

Alloying/Assaying Fixture

Figure 1:
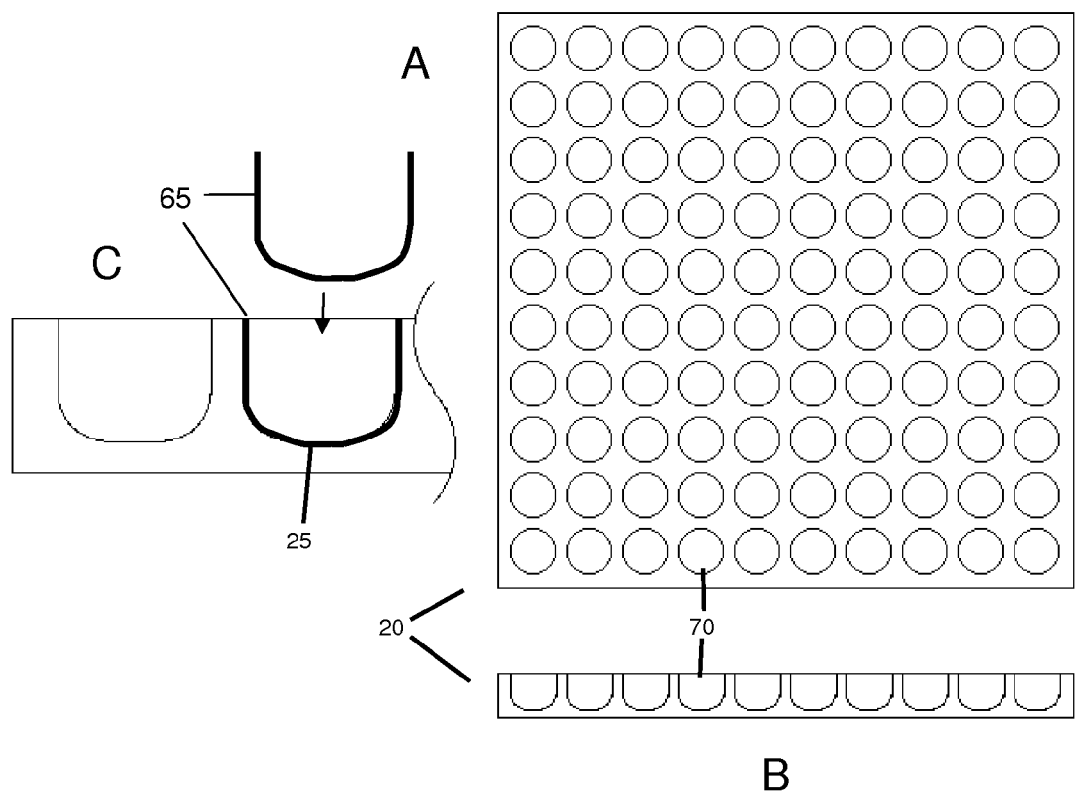
FIG. 1A shows a top view of a multiwell plate 20.
FIG. 1B shows a cross-sectional view of the multiwell plate.
FIG. 1C shows an enlargement of the cross-sectional view.

In a first embodiment, the invention provides a fixture that can be used both for high-throughput ball milling and for assaying alloys that are produced through the ball milling process. The fixture includes a multiwell plate, a multiwell plate lid, and a cap. FIGS. 1A and 1B show a top view and a cross-sectional view, respectively, of one embodiment of a suitable multiwell plate 20. The multiwell plate typically is a planar structure having a top, a bottom and a plurality of sample wells 70. Each of the sample wells has one or more sidewalls and a bottom wall. Although schematically depicted in, e.g., FIG. 1 as having a substantially cylindrical shape (i.e., a circular cross-section), sample wells can have other cross-sectional shapes. To illustrate, at least a segment of a sample well can have a cross-sectional shape independently selected from, e.g., a regular n-sided polygon, an irregular n-sided polygon, a triangle, a square, a rounded square, a rectangle, a rounded rectangle, a trapezoid, a circle, an oval, or the like. Rounded internal reaction well surfaces are generally preferred to reduce undesirable accumulation of materials that can occur at angled internal wall surfaces. Rounded edges typically join the sidewall(s) to the bottom wall, thereby forming a concave sample well bottom 25 as illustrated in FIG. 1B.

Figure 2A:
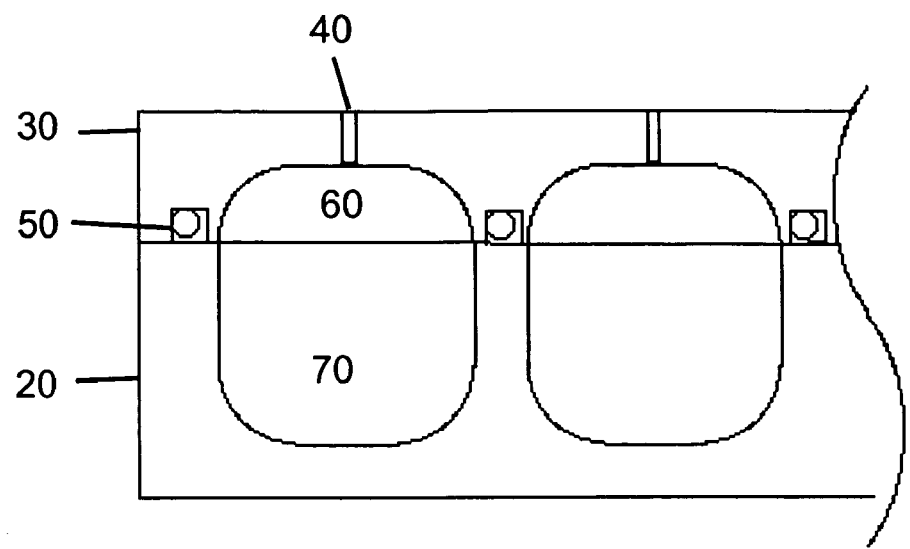
FIGS. 2A and 2B show cross-sectional views of a multiwell plate 20 with an attached lid 30.
Figure 2B:
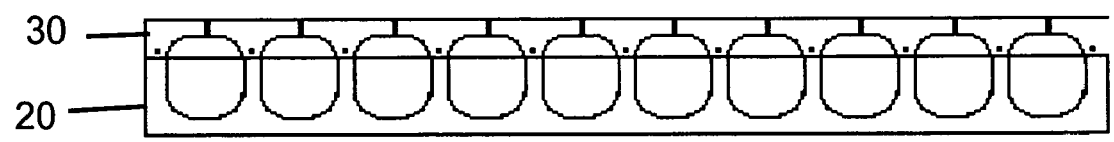

The lid defines a planar expanse that is of sufficient size to cover the sample wells when the lid is placed on the multiwell plate. A suitable lid 30 is illustrated in FIGS. 2A and 2B. The lid has a bottom surface that, in preferred embodiments, has a plurality of recessed areas 60 that generally have shapes corresponding to inner cross-sectional shapes of the sample wells 70 of the multiwell plates 20. Preferably, each of these recessed areas has a diameter equal to that of the sample wells. The recessed areas are arrayed on the bottom surface such that each recessed area is aligned with a sample well when the lid is placed on the multiwell plate. In some embodiments, the recessed areas have a concave radius of curvature that is similar to, or identical to, that of the bottom of the sample wells of the multiwell plate. This prevents packing of powders into cracks during the ball milling process.

The lids have a plurality of gas outlet ports 40 that allow gas flow into and out of each sample well when the lid is positioned on the multiwell plate. In preferred embodiments, each sample well is in fluid communication with at least one gas outlet port when the lid is placed on the multiwell plate.

Figure 3A:
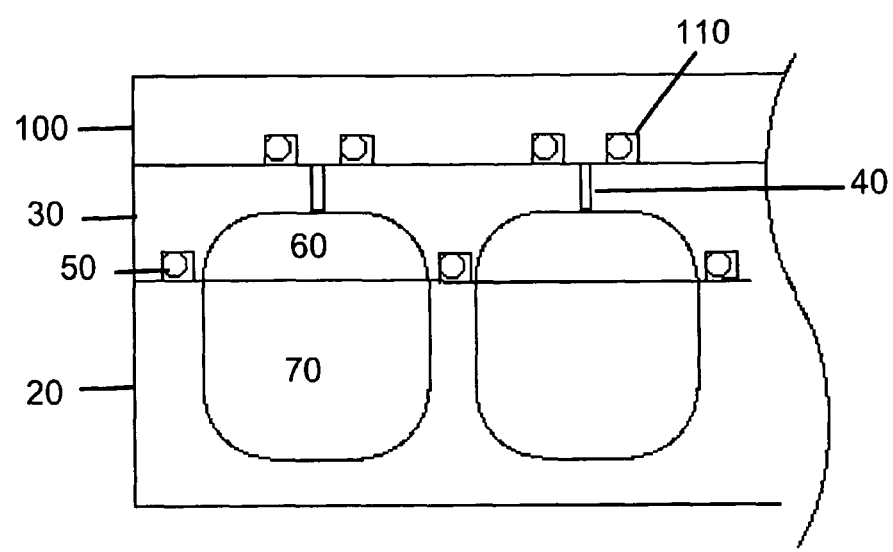
FIGS. 3A and 3B show cross-sectional views of a multiwell plate 20, attached lid 30, and cap 100.
Figure 3B:
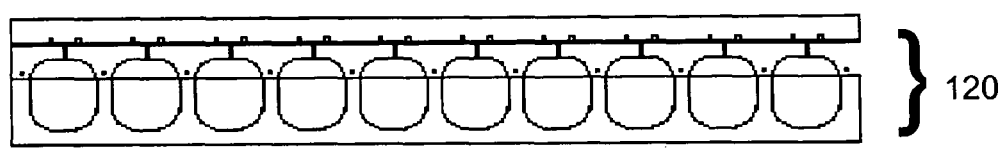

As shown in FIGS. 3A and 3B, the alloying/assay fixtures 120 also typically include a cap 100 that is positioned on the lid 30. The cap defines a planar expanse sufficient to cover each of the plurality of gas outlet ports when the cap is positioned on the lid, thereby preventing gas flow into or out of the sample well via the gas outlet ports 40.

The components of the high-throughput ball milling fixture are composed of any suitable material that can maintain the structural integrity of the fixture during the ball milling procedure. For example, one or more of the fixture components can be composed of metal, plastic, ceramic, or any suitable composite. Stainless steel is an example of a preferred material for the multiwell plate, lid, and caps of the high-throughput ball milling fixtures of the invention. In some embodiments, the sample wells are lined with a material such as stainless steel, carbon steel, tungsten carbide, ceramics, or other suitable materials known to those of skill in the art (65, as shown in FIG. 1C).

The high-throughput ball milling fixture generally has one or more seals disposed between the multiwell plate and the lid. The seals allow gas to flow between a sample well and an associated gas outlet port in the lid, but prevent gas flow between sample wells and between a sample well and a non-associated gas outlet port. The seals can be, for example, O-rings 50 as shown in FIG. 2A. Similarly, the fixture typically includes one or more seals disposed between the lid and the cap, which seals prevent gas from flowing from one gas outlet port to another. The use of O-rings 110 as such seals is illustrated in FIG. 3A. In other embodiments, the seals are sheets of gasketing material that have perforations which correspond to the sample wells and/or to the conduit positions. In particular, gasket sheets or O-rings suitable for use in the devices of the present invention are optionally made from essentially any chemically resistant rubber or elastomeric material, many of which are well known in the art. For example, gasket sheets and O-rings are optionally fabricated from, e.g., silicone rubber, Viton®, Santoprene®, Teflon®, Gore-Tex®, Celerus™, or the like. Many of these materials are readily available from various commercial suppliers, such as W.L. Gore & Associates (Newark, Del.). Combinations of materials, e.g., in the form of laminates are also optionally utilized as seals in the devices of the invention.

High-throughput Ball Milling Apparatus

The invention also provides a high-throughput ball milling apparatus that is configured for massively parallel ball milling operations. In some embodiments, the apparatus can simultaneously perform ball milling operations on hundreds or even thousands of different mixtures, yielding many different alloy mixtures that can then be tested to identify those that have desired properties.

The apparatus typically includes: (a) a rotary platform which rotates about a first axis; (b) a plurality of receptacles that are rotatably supported on the rotary platform, wherein each receptacle rotates about an axis that is substantially parallel to the first axis and is configured to hold at least one multiwell ball milling fixture; and (c) a motor or other drive means that causes the rotary platform and the receptacles to rotate.

Figure 6:
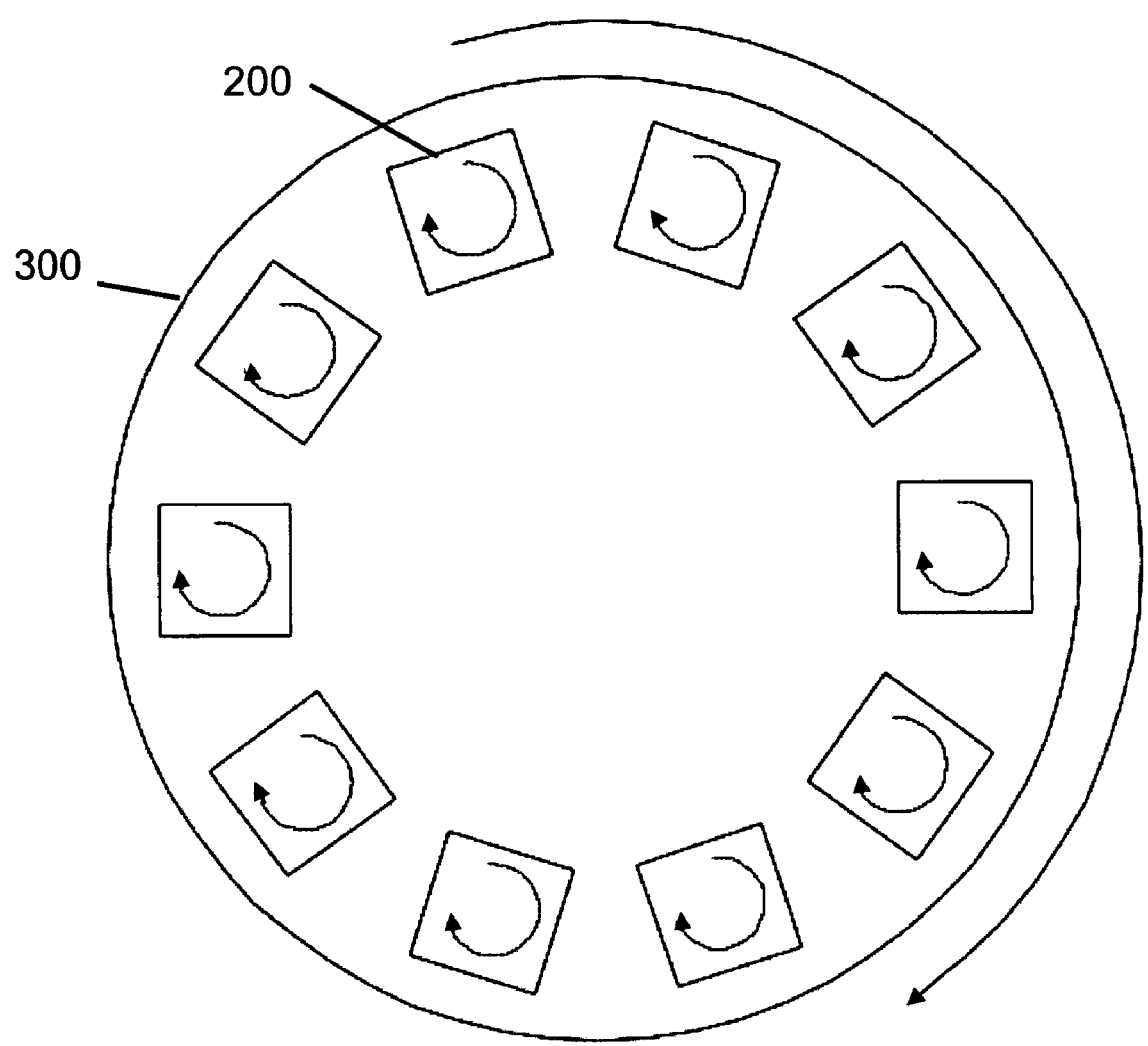
FIG. 6 shows a top view of a rotary platform 300 to which are attached ten rotating receptacles 200.

The high-throughput ball milling apparatus has, as illustrated in FIG. 6, at least one rotary platform 300 that rotates about a first axis. The rotary platform is typically supported on a main shaft. In some embodiments, the apparatus has two or more rotary platforms, each of which holds multiple receptacles for sample containers. Thus, the use of multiple rotary platforms allows a greater number of ball milling operations to be simultaneously performed. In some embodiments, the apparatus has two or more rotary platforms that are stacked one above the other, each supported by the same main shaft.

The apparatus generally has at least two, and preferably four or more receptacles, and in some embodiments ten or more receptacles for attaching multiwell ball milling fixtures to the rotary platform. The receptacles 200, as shown in FIG. 6, are rotatably supported on the rotary platform, generally near the outer perimeter of the rotary platform. Each receptacle can spin about its own axis, which axis is generally parallel to the axis of rotation of the rotary platform.

Figure 7:
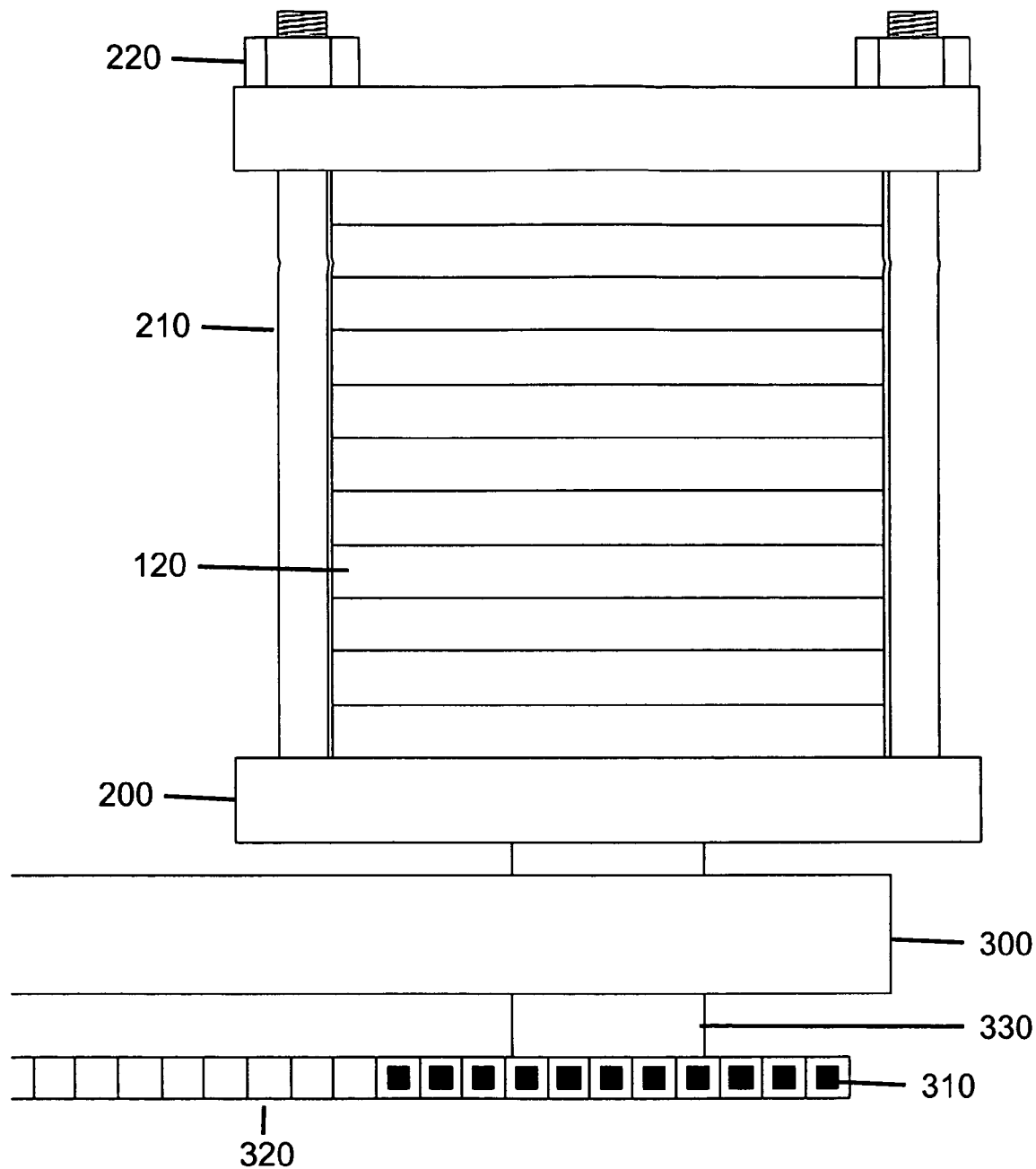
FIG. 7 shows a partial side view of a high-throughput ball milling apparatus of the invention.

The receptacles, an embodiment of which is illustrated in FIG. 7, are each configured to hold at least one multiwell ball milling fixture 120, each of which typically includes a multiwell plate and a lid. The multiwell ball milling fixtures can also include a cap attached to the lid. In some embodiments, each receptacle can hold two or more, five or more, or even ten or more multiwell ball milling fixtures. FIG. 7 shows eleven multiwell ball milling fixtures attached to a single receptacle (the figure shows the multiwell plate and its associated lid as a single unit). The multiwell ball milling fixtures are typically attached to the receptacles so that the multiwell ball milling fixtures remain in place during rotation of the receptacles and/or the rotary platform. The multiwell ball milling fixtures are retained in position by fasteners such as clamping mechanisms, bolts, or other attachment means known to those of skill in the art. In the particular embodiment illustrated in FIG. 7, the ball milling fixtures are held in place by a retention plate 210 that is fastened to the rotating receptacle 200 by bolts 210 and nuts 220.

In some embodiments, the receptacles are configured to hold one or more alloying/assay fixtures such as those described herein. The use of these alloying/assay fixtures, including the multiwell plates with attached lids and caps, allows one to perform the ball milling and subsequent assaying in the same containers. This minimizes the manipulations that are required, as well as reducing losses due to transferring the powders from one container to another.

Massively parallel ball milling is accomplished by using multiple receptacles, each of which holds multiple sample containers, each of which in turn has multiple wells. For example, in some embodiments that high-throughput ball milling apparatus can have ten receptacles attached to a rotary platform, with each receptacle holding ten multiwell ball milling fixtures, each of which has 100 wells. This apparatus can simultaneously carry out ten thousand ball milling operations.

The high-throughput ball milling apparatus of the invention also typically includes a motor or other means for driving the rotation of the rotary platform, and also for driving the rotation of the receptacles. Suitable motors are known to those of skill in the art and include, e.g., electric motors, internal combustion engines, turbines, and the like.

The motor or other drive means typically drives the rotation of the rotary platform through drive mechanisms such as gears, chains, belt drives, and the like. Speed changing devices can also be included. The rotating receptacles can be driven by one or more additional motors, or can be driven by the same motor as which drives rotation of the rotary platform. Again, gears, chains, belt drives, and the like, with or without speed changing devices, are suitable for transferring the motor force to the rotating receptacles. FIG. 7 illustrates an example of a drive mechanism for a rotating receptacle 200 which is attached to a rotating platform 300 by a shaft 330. Shown is one receptacle 200 for multiwell plates 20 that is attached to a rotary platform 300 by a shaft 330. A sprocket 310 is driven by a chain 320 that is connected to a sprocket on the motor. U.S. Pat. No. 6,126,097 includes a discussion of various configurations of drive mechanisms for ball milling apparatuses that are suitable for use in the high-throughput ball milling apparatus of the invention.

In some embodiments, the high-throughput ball milling apparatus is configured to allow the rotational speed of the rotary platform to be set independently of that of the receptacles. This permits the rotational speeds to be adjusted independently to optimize the ball milling process.

High-throughput Ball Milling Process

The high-throughput ball milling apparatus of the invention can be used for preparing large numbers of alloys or other materials in a very fine powder form. The materials to be alloyed are deposited in sample wells of the multiwell plates. These materials are generally in micron- or millimeter-sized starting powders, which are reduced to nanometer-scaled powders by the ball milling process. In some embodiments, combinations of different materials, and/or different amounts of materials are placed in each well. The materials can be arrayed in combinatorial fashion.

An example of an apparatus for dispensing powders in a combinatorial, high-throughput manner is shown in FIG. 4. This apparatus can be used to dispense mixtures of powders into the sample wells 70 of the high-throughput ball milling fixtures 20 described herein. The apparatus includes a dispensing head that includes one or more dispensing tips 350. Each dispensing tip is fluidly connected to a reservoir 360 that contains an element or other compound to be used as a precursor substance. The precursor compound is generally suspended in a liquid 390 and can be maintained in suspension by stirring using a motor-driven stirrer 370, if desired. A pump 380 can be used to transfer the precursor compounds to the dispensing tip. A multichannel pump connected to multiple reservoirs, each of which contains a different precursor substance, can be used in conjunction with a controller that directs the amounts and particular combinations of precursor substances to be dispensed into each sample well.

If the materials are suspended in a liquid for dispensing into the sample wells, the liquid is preferably evaporated from the wells prior to conducting the ball milling operation. It is possible, however, to perform the ball milling on wet samples if desired.

Suitable precursor substances for mechanical alloying can include any element or compound. The precursor substances are typically provided in a particulate form to facilitate distribution into the sample wells. To obtain alloys that exhibit hydrogen storage capability, elements that can form a compound with hydrogen can be used as one of the precursor substances. Such elements include, for example, Li, Be, Mg, Ti, V, and Zr. Other suitable precursor substances for forming hydrogen-adsorbing alloys include, for example, C, B, Si, P, Zn, Ni, Fe, Cr, Cu, Al, Ca, Na, and K.

Grinding balls are also placed in the sample wells, either before or after the precursor substances are added to the wells. Grinding balls suitable for use in ball milling operations are known to those of skill in the art, and can be formed of materials such as stainless steel, carbon steel, tungsten carbide, ceramics, and the like. The diameter of the grinding balls is typically at least one mm, and often two mm or greater. The maximum grinding ball diameter is generally fifty mm, more typically about 10 mm. In some embodiments, the balls have a diameter of between about 2 and 5 mm.

Figure 5:
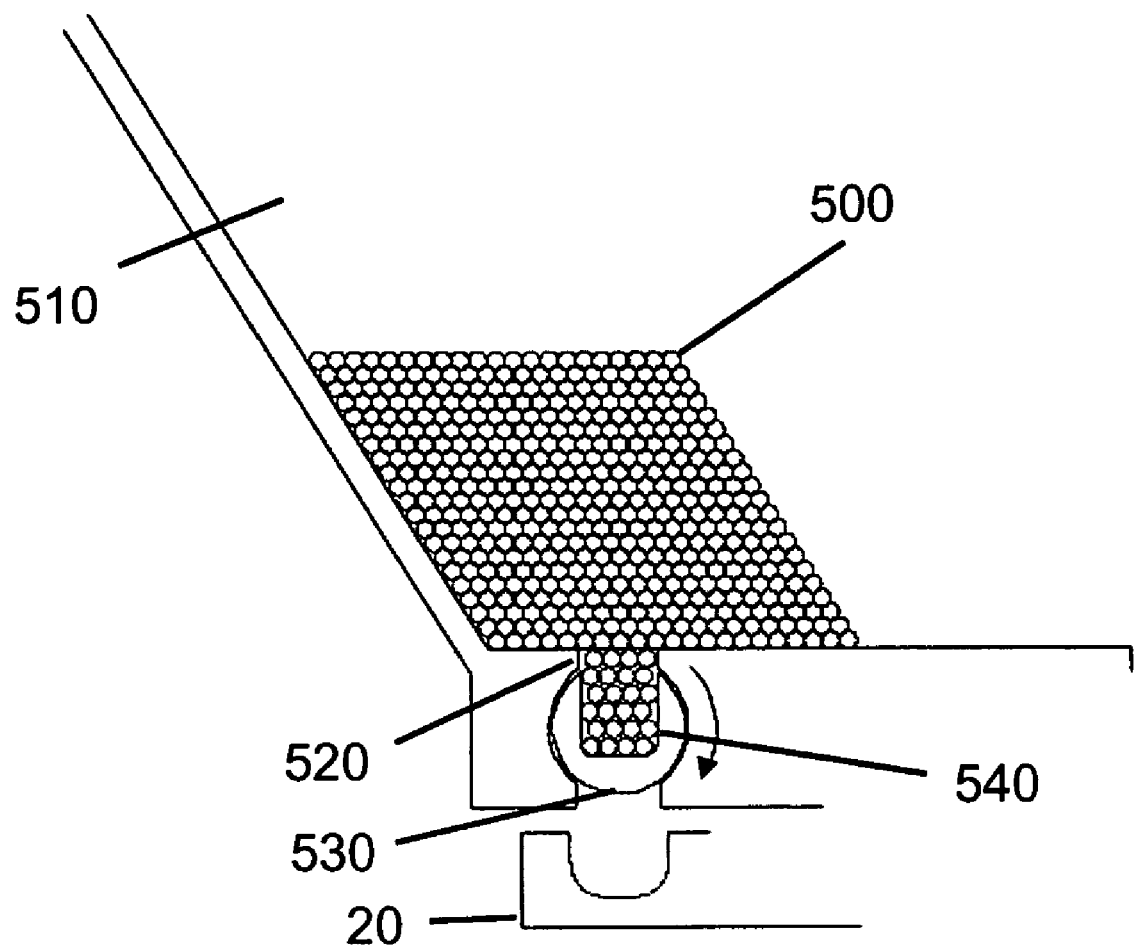
FIG. 5 shows a device for dispensing balls into individual wells of a multiwell plate 20.

An example of an apparatus that is useful for dispensing grinding balls 500 to wells of a multiwell plate 20 is shown in FIG. 5. The grinding balls to be dispensed are placed in a reservoir 510 that has one or more openings 520 in the bottom surface. The opening is occluded by a round (cylindrical or spherical) rotating element 530 that has a recessed area 540. When the rotating element is rotated so that the recessed area is aligned with the top of the opening in the bottom surface of the reservoir, the grinding balls fill the recessed area. The rotating element is then rotated so that the recessed area is aligned with the bottom of the opening, thereby dispensing the grinding balls into the sample wells. In some embodiments, the dispensing apparatus has multiple openings so that grinding balls can be dispensed simultaneously into multiple wells of a multiwell plate. In preferred embodiments, the dispensing apparatus has a number of openings that is equal to the number of rows or columns of wells of the multiwell plate, with the openings having a spatial position that corresponds to that of the spacing of the multiwell plate wells. In other embodiments, the dispensing apparatus has a number of openings that equals the number of wells of the multiwell plate, with the spatial distribution of the openings corresponding to that of the sample wells. In such embodiments in which the dispensing apparatus has multiple openings, the rotating elements can be one or more cylindrical elements that extend through the dispensing apparatus with an axis of rotation that is parallel to the plane of the bottom surface of the reservoir. These cylindrical elements have a plurality of recessed areas that correspond in number and position to the openings in a row or column.

Once the materials to be alloyed and the grinding balls are present in the sample wells, a lid is attached to the multiwell plate to seal the sample wells. If the lid has gas outlet ports, as described above for the lid of the alloying/assaying fixture of the invention, a cap is attached to the lid to seal the gas outlet ports.

The multiwell plates with attached lids are then attached to a rotating receptacle of a high-throughput ball milling apparatus of the invention. The ball milling process is run for a sufficient time to achieve the desired average particle size. In typical embodiments, the rotating platform rotates at a speed of 50-500 rpm, more typically between about 50 and 100 rpm. The rotating receptacles can rotate at the same speed as the rotating platform, or at a different speed. For example, in some embodiments the receptacles rotate at a speed of between 20 and 500 rpm, more typically between about 50 and 100 rpm. Using the apparatus, one can obtain materials having an average particle size of less than 10 μm in diameter, more preferably less one μm or less than 100 nm, and in some embodiments less than 10 nm in diameter. Materials that are in the form of powders having such particle sizes are sometimes referred to herein as being in an ultrafine powder form.

For certain applications, it is desirable to conduct the ball milling operation and/or other operations involving the resulting mechanical alloy in an inert atmosphere. The entire apparatus can be positioned in an airtight enclosure in which the atmosphere is composed of an inert gas. Alternatively, the atmosphere in the sample wells can be replaced with the inert gas. Suitable inert gases that can be used include, for example, helium, neon, argon, krypton, xenon, and mixtures thereof.

High-throughput Gas Storage Assay Apparatus

The invention also provides devices for massively parallel assays of the gas storage capacity of various materials, such as alloys. This invention is useful, for example, to assay the hydrogen storage capacity of ultra-fine particles of materials such as metals, hydrides, and the like. The assay apparatus of the invention provides a means for conducting a large number of gas storage assays simultaneously, thereby making feasible the assay of combinatorial collections of materials in a high throughput manner.

A gas storage assay cap for a multiwell plate is provided. The assay cap has a plurality of gas outlet ports that each has a first opening on the bottom surface of the assay cap and a second opening in a second surface (e.g., the top surface or a side surface) of the cap. In some embodiments, the gas storage assay caps have a planar expanse that is sufficient to cover the sample wells of a multiwell plate when the cap is positioned on the plate. The first openings of the gas outlet ports are spatially arranged such that each gas outlet port is in fluid communication with a sample well of a multiwell plate when the assay cap is positioned on the multiwell plate.

Figure 8:
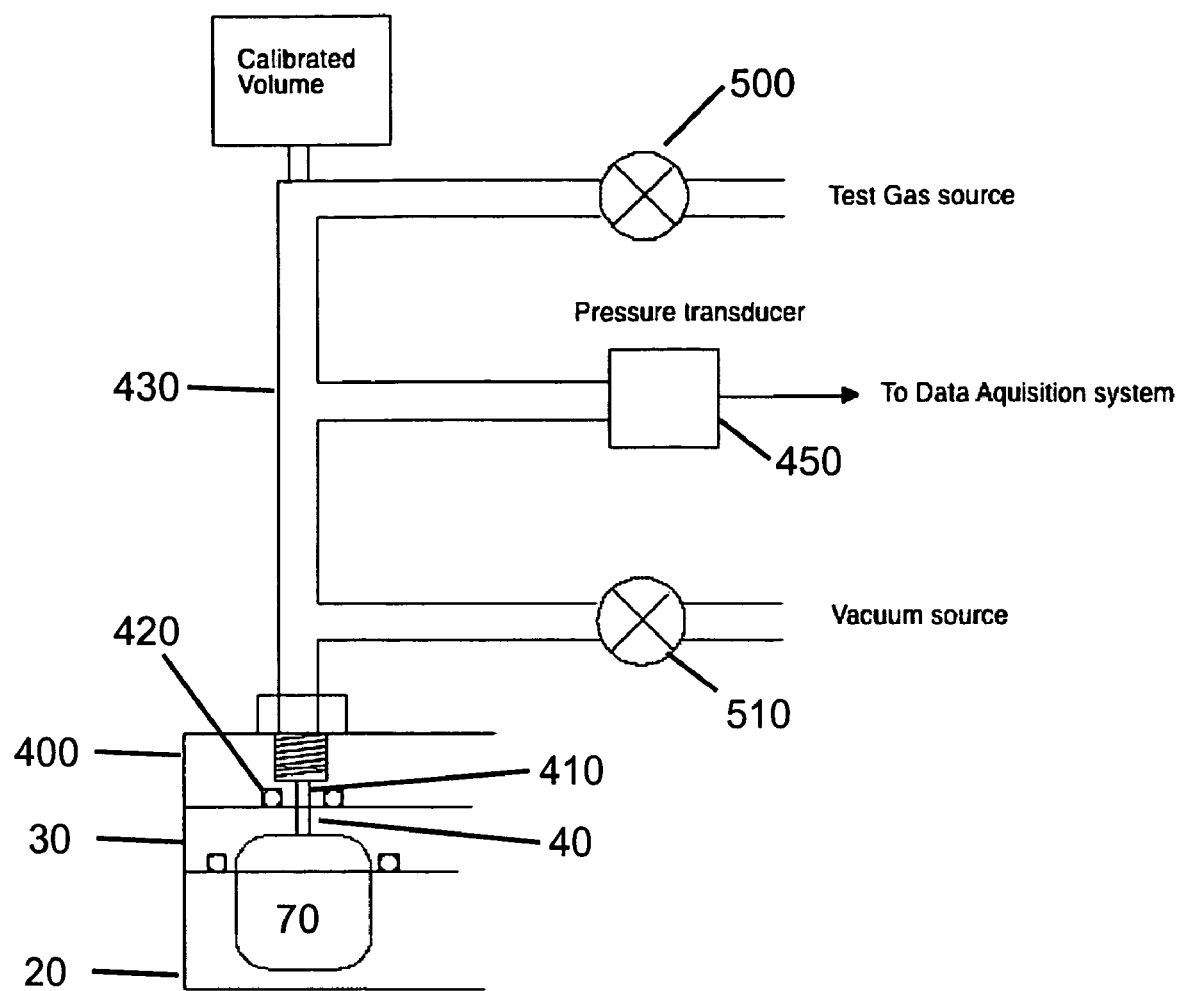
FIG. 8 shows a schematic of a high-throughput gas storage assay device.

In other embodiments, as illustrated in FIG. 8, the gas storage assay caps are configured to be placed on a lid 30 that in turn is placed on a multiwell plate 20. The assay caps have a planar expanse that is sufficient to cover the gas outlet ports 40 of the lid when the caps are placed on the lid. The gas outlet ports 410 of the assay cap are spatially positioned to be in fluid communication with corresponding gas outlet ports of the lid and therefore are also in fluid communication with a sample well 70 of a multiwell plate when the lid is positioned on the plate and the cap is positioned on the lid.

The gas storage assay caps of the invention also include a pressure sensor 450 in fluid communication with the second opening of each of at least one of the gas outlet ports. A tube or other conduit can be used to connect the pressure sensor to the opening of the gas outlet port. Typically, each gas outlet port is in fluid communication with a pressure sensor. Suitable pressure sensors are known to those of ordinary skill in the art, and include, for example, pressure transducers.

The gas outlet ports of the assay caps are in fluid communication with a test gas source. The gas source can be connected to the gas outlet port by a tube or other conduit 430, for example. In some embodiments, the gas source is connected to each of the gas outlet ports by means of a distribution manifold or the like. The test gas source contains the gas for which one desires to assay the storage capacity of a material that is contained in the multiwell plates. For example, the test gas source can contain hydrogen, oxygen, or any other gas of interest. A valve 500 (e.g., a solenoid valve) that is structured to regulate gas flow to and from the test gas source is operably connected to the test gas source.

The gas outlet ports are also in fluid communication with a vacuum source. The vacuum source can be connected to the gas outlet ports by a tube or other conduit, which conduit can be the same as or different from the conduit that connects the gas source to the gas outlet ports. The apparatus generally also includes a valve 510 (e.g., a solenoid valve) that can turn on or off the application of a vacuum to the gas outlet ports. In some embodiments, a single valve switches between the test gas source, the vacuum source, and the pressure sensor being in fluid communication with the gas outlet port. Although the drawings illustrate a single gas outlet port providing fluid communication between a sample well and the test gas source, the vacuum source, and the pressure sensor, the gas storage assay caps of the invention can also have two or more gas outlet ports for each sample well. In these embodiments, the gas source, the vacuum source, and the pressure sensor can each be connected to an individual gas outlet port if desired.

The invention also provides high throughput gas storage assay devices for conducting multiple assays of gas storage capacity. These devices include a multiwell plate that has a plurality of sample wells. The materials to be assayed for gas storage capacity are placed in the sample wells. The devices also include a lid that defines a planar expanse sufficient to cover the sample wells of the multiwell plate. The lid has a plurality of gas outlet ports that are positioned such that two or more of the sample wells are each in fluid communication with an associated gas outlet port when the lid is positioned on the multiwell plate. In some embodiments, each sample well is in fluid communication with an associated gas outlet port.

The assay devices also typically include an assay cap such as that described above. The assay cap defines a planar expanse sufficient to cover the gas outlet ports of the lid when the assay cap is positioned on the lids. The assay cap has a plurality of gas outlet ports that are positioned such that at least one gas outlet port in the cap is in fluid communication an associated gas outlet port in the lid.

Typically, one or more seals 420 are disposed between the lid and the assay cap (or between the multiwell plate and the assay cap, if the assay cap is positioned directly on the multiwell plate), which seals allow gas to flow between a sample well and an associated gas outlet port but prevent gas flow between two or more sample wells and between a sample well and a gas outlet port other than that which is associated with that sample well.

In some embodiments, the assay devices use the multiwell alloying/assay fixtures described above. The assay caps are attached to the alloying/assay fixtures for conducting the gas storage assay.

The gas storage assay devices of the invention can also include a controller that has logic instructions that direct the device to perform a gas storage assay as described below.

High-throughput Gas Storage Assay Methods

The invention also provides methods for conducting high-throughput assays of the gas storage capacity of materials. The methods are useful, for example, to assay the gas storage capacity of alloys that have been formed through use of the high-throughput ball milling apparatus described herein, although materials formed by other means can also be assayed for gas storage capacity using the high-throughput gas storage assay methods and devices of the invention.

If the materials to be assayed have been formed using the multiwell ball milling fixture described herein, any solvents that are present in the sample wells after the ball milling is removed by evaporation (after removing the cap, if attached). The ball milling fixture can be heated to facilitate the evaporation. It is not necessary to remove the powders from the ball milling fixture in some embodiments, as the other components of the gas storage assay devices are configured to attach to the same multiwell plate and lid as are used in the ball milling operation.

The assays are conducted using a gas storage assay device as described above. The assay cap is attached to the multiwell plate (which may or may not have an attached lid). A vacuum is applied to the sample wells, for example by opening a valve between the gas outlet ports and the vacuum source. The vacuum source evacuates each well and the associated gas outlet ports and conduits. The vacuum valve is then closed and the valve which regulates flow from the test gas source is opened, thereby allowing the test gas to flow into the sample wells. The test gas source valve is then closed, creating a static volume of test gas at a fixed pressure in each well. The gas pressure in each well is determined using the pressure sensors. Preferably, readings from the pressure sensors are automatically monitored over the time of the assay.

The methods are useful for determining various gas storage properties of the materials in the sample wells. A decrease in pressure in a particular well over time is a measure of the gas absorption capacity of the material in that well. Gas desorption can be assayed subsequently by raising the temperature of the sample and monitoring for an increase in gas pressure in a well. By performing the adsorption/desorption experiments at varying temperatures, one can determine the energy required to load and unload hydrogen or other gases from the alloys. The number of gas loading and unloading cycles that a particular material can undergo before loss of desirable properties can be determined by repeating the adsorption/desorption assay numerous times.

The use of the high throughput gas storage assay device allows many samples to be tested in a rapid automated manner. In some embodiments, ten or more samples are tested in a single experiment. In preferred embodiments, 100 or more, or 1,000 or more samples are tested in a single experiment using the devices of the invention. In fact, hundreds of thousands or even millions of different materials can be assayed using the methods and devices of the invention. Computer algorithms for analyzing results of combinatorial studies can be used to analyze the results of the assays and facilitate the identification of an alloy having optimal gas storage properties. See, e.g., U.S. Pat. No. 6,826,549. Materials that exhibit promising gas storage properties can be subjected to further tests using other assays known to those of skill in the art.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A multiwell ball milling fixture consisting essentially of a multiwell plate, a cap, at least one seal, and a lid, wherein:
   (a) the multiwell plate comprises a plurality of sample wells that comprise a liner, wherein each sample well is formed within the thickness of the multiwall plate so that the top of each sample well opens into the upper surface of the multiwall plate, and further wherein each sample well further comprises a sidewall and a bottom surface, wherein the bottom surface is joined to the sidewall by a rounded edge;
   (b) the lid defining a planar expanse sufficient to cover the sample wells, which lid comprises (i) a plurality of recessed areas which have a cross-sectional shape that corresponds to the cross-sectional shape of the sample wells, and the positions of which recessed areas spatially correspond to the sample wells when the lid is placed on the multiwell plate, said recessed area comprise a top surface that is concave relative to the planar expanse of the lid, and (ii) a plurality of gas outlet ports, wherein the gas outlet ports are positioned such that two or more of the sample wells are each in fluid communication with an associated gas outlet port when the lid is positioned on the multiwell plate and the fixture does not include a sizing screen; and
   (c) the cap defines a planar expanse sufficient to cover each of the plurality of gas outlet ports when the cap is positioned on the lid,
   wherein the sample wells are sealed when the lid and cap are attached to the multiwell plate.

2. The multiwell ball milling fixture of claim 1, wherein the at least one seal further comprises one or more seals disposed between the multiwell plate and the lid, which seals allow gas flow between a sample well and an associated gas outlet port but prevent gas flow between sample wells and between a sample well and a non-associated gas outlet port.

3. The multiwell ball milling fixture of claim 2, wherein the seals comprise O-rings.

4. The multiwell ball milling fixture of claim 1, wherein the at least one seal further comprises one or more seals disposed between the lid and the cap, which seals prevent gas flow from one gas outlet port to a second gas outlet port associated with a second sample well.

5. The multiwell ball milling fixture of claim 1, wherein the recessed areas have a diameter that is the same as the diameter of the sample wells.

6. The multiwell ball milling fixture of claim 1, wherein the concave top surface of the recessed areas has a radius of curvature that is identical to the radius of the rounded edge that joins the sidewall and the bottom surface of the multiwell plate.

7. The multiwell ball milling fixture of claim 1, wherein either or both of the multiwell plate and the lid are constructed of stainless steel.

8. The multiwell ball milling fixture of claim 1, wherein the sample wells contain an inert gas.

9. The multiwell ball milling fixture of claim 1, wherein the liner comprises a material selected from the group consisting of stainless steel, carbon steel, tungsten carbide and ceramics.

10. The multiwell ball milling fixture of claim 1, wherein the lid comprises a plurality of recessed areas which have a cross-sectional shape that corresponds to the cross-sectional shape of the sample wells, and the positions of which spatially correspond to the sample wells when the lid is placed on the multiwell plate.

11. The multiwell ball milling fixture of claim 10, wherein the recessed areas comprise a top surface that is concave relative to the planar expanse of the lid.

* * * * *

UNITED STATES PATENT AND TRADEMARK OFFICE
CERTIFICATE OF CORRECTION

| | | |
|---|---|---|
| PATENT NO. | : 7,767,151 B2 | Page 1 of 1 |
| APPLICATION NO. | : 11/197180 | |
| DATED | : August 3, 2010 | |
| INVENTOR(S) | : Robert Charles Downs | |

It is certified that error appears in the above-identified patent and that said Letters Patent is hereby corrected as shown below:

Col. 11, line 27, cancel the text beginning with "1. A multiwell balling fixture" to and ending "the multiwell plate" in col. 12, line 8, and insert the following claim:
    --1. A multiwell ball milling fixture consisting essentially of a multiwell plate, a cap, at least one seal and a lid, wherein:
(a) the multiwell plate comprises a plurality of sample wells that comprise a liner, wherein each sample well is formed within the thickness of the multiwell plate so that the top of each sample well opens into the upper surface of the multiwell plate, and wherein each sample well further comprises a sidewall and a bottom surface, wherein the bottom surface is joined to the sidewall by a rounded edge;
(b) the lid defining a planar expanse sufficient to cover the sample wells, which lid comprises a plurality of gas outlet ports, wherein the gas outlet ports are positioned such that two or more of the sample wells are each in fluid communication with an associated gas outlet port when the lid is positioned on the multiwell plate and the fixture does not include a sizing screen; and
(c) the cap defines a planar expanse sufficient cover each of the plurality of gas outlet ports when the cap is positioned on the lid,
wherein the sample wells are sealed when the lid and cap are attached to the multiwell plate.--

Col. 12, line 25, cancel the text beginning with "6. The multiwell balling fixture of claim 1" to and ending "the multiwell plate", and insert the following claim:
    --6. The multiwell ball milling fixture of claim 1, wherein the top surface of the recessed areas have a concave radius of curvature that is similar to or identical to the radius of the rounded edge that joins the sidewall and the bottom surface of the multiwell plate.--

Signed and Sealed this
Seventeenth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,767,151 B2 | |
| APPLICATION NO. | : 11/197180 | |
| DATED | : August 3, 2010 | |
| INVENTOR(S) | : Robert Charles Downs | |

It is certified that error appears in the above-identified patent and that said Letters Patent is hereby corrected as shown below:

Col. 11, line 27, cancel the text beginning with "1. A multiwell balling fixture" to and ending "the multiwell plate" in col. 12, line 8, and insert the following claim:

--1. A multiwell ball milling fixture consisting essentially of a multiwell plate, a cap, at least one seal and a lid, wherein:
(a) the multiwell plate comprises a plurality of sample wells that comprise a liner, wherein each sample well is formed within the thickness of the multiwell plate so that the top of each sample well opens into the upper surface of the multiwell plate, and wherein each sample well further comprises a sidewall and a bottom surface, wherein the bottom surface is joined to the sidewall by a rounded edge;
(b) the lid defining a planar expanse sufficient to cover the sample wells, which lid comprises a plurality of gas outlet ports, wherein the gas outlet ports are positioned such that two or more of the sample wells are each in fluid communication with an associated gas outlet port when the lid is positioned on the multiwell plate and the fixture does not include a sizing screen; and
(c) the cap defines a planar expanse sufficient to cover each of the plurality of gas outlet ports when the cap is positioned on the lid,
wherein the sample wells are sealed when the lid and cap are attached to the multiwell plate.--

Col. 12, line 25, cancel the text beginning with "6. The multiwell balling fixture of claim 1" to and ending "the multiwell plate", and insert the following claim:
--6. The multiwell ball milling fixture of claim 1, wherein the top surface of the recessed areas have a concave radius of curvature that is similar to or identical to the radius of the rounded edge that joins the sidewall and the bottom surface of the multiwell plate.--

This certificate supersedes the Certificate of Correction issued January 17, 2012.

Signed and Sealed this
First Day of May, 2012

David J. Kappos
*Director of the United States Patent and Trademark Office*